(12) United States Patent
Zhou et al.

(10) Patent No.: US 7,106,429 B2
(45) Date of Patent: Sep. 12, 2006

(54) APPARATUS AND METHOD FOR DETECTING CHANGE OF DIELECTRIC CONSTANT

(75) Inventors: Zhiping Zhou, Marietta, GA (US); Kimsey T. Pollard, Lawrenceville, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 404 days.

(21) Appl. No.: 10/766,359

(22) Filed: Jan. 27, 2004

(65) Prior Publication Data

US 2005/0162656 A1    Jul. 28, 2005

(51) Int. Cl.
*G01N 21/41* (2006.01)
(52) U.S. Cl. .................... 356/128; 356/133
(58) Field of Classification Search ............. None
See application file for complete search history.

(56) References Cited

U.S. PATENT DOCUMENTS

| | | | |
|---|---|---|---|
| 4,240,747 A | * 12/1980 | Harmer | 356/133 |
| 4,950,074 A | * 8/1990 | Fabricius et al. | 356/133 |
| 5,173,747 A | * 12/1992 | Boiarski et al. | 356/481 |
| 5,377,008 A | * 12/1994 | Ridgway et al. | 356/481 |
| 5,663,790 A | * 9/1997 | Ekstrom et al. | 356/128 |

* cited by examiner

*Primary Examiner*—Michael P. Stafira
(74) *Attorney, Agent, or Firm*—Todd Deveau; Thomas, Kayden, Horstemeyer & Risley LLP

(57) ABSTRACT

Disclosed herein is an apparatus and method for detecting a selected material that change an effective dielectric constant of a circular resonator. An example of the apparatus includes an input waveguide, an output waveguide and a circular resonator. The input waveguide receives electromagnetic wave from an electromagnetic wave source. The circular resonator is located adjacent to the input and output waveguides, which enables the resonator to receive electromagnetic wave from the input waveguide. The circular resonator bonds to a selected material, e.g. chemical gas, chemical liquid, and bio-agent. The selected material can change the effective dielectric constant of the circular resonator, which in turn causes a change in the electromagnetic wave intensity of the circular resonator. The output waveguide receives the change in electromagnetic wave intensity from the circular resonator, which can be used to determine the selected material qualitatively and quantitatively.

36 Claims, 7 Drawing Sheets

APPARATUS AND METHOD FOR DETECTING CHANGE OF DIELECTRIC CONSTANT

TECHNICAL FIELD

The present disclosure is generally related to detecting gaseous, liquid and solid materials, more particularly, an apparatus and method for sensing a selected material such as chemical substances and bio-agents by detecting a change in the power of the electromagnetic wave in a circular resonator when the circular resonator is exposed to the selected material.

BACKGROUND

Generally, ring resonators have been known and used to select an electromagnetic wavelength. In addition, ring resonators can be used to sense chemical substances and bio-agents. The advantage of using ring resonators is that when provided with energy of electromagnetic wave or light, a resonance condition can be established and can be determined.

U.S. Pat. No. 5,663,790, to Eckstrom, et al., utilizes the resonance condition of the ring resonator for determining the refractive index of the ring resonator, which can be used to determine the quality and quantity of a sample. Eckstrom appears to disclose an apparatus and method for sensing sampled materials that includes a first ring resonator for sensing sampled materials and a second ring resonator for sensing referenced materials. The apparatus further includes a straight waveguide for inputting light. The straight waveguide also senses a change in wavelengths of the light from first and second resonators that are exposed to the sampled materials and referenced materials, respectively. The change in wavelength of the light caused by the referenced materials and the sampled materials can be processed to determine the refractive index of the ring resonator.

The index of refraction is a specific expression of a dielectric constant in optical wavelength range. Thus, the measurement of index refraction utilizes only a small spectrum of electromagnetic wave in order to measure the change in optical wavelength.

From the above, it can be appreciated that it would be desirable to have an apparatus and method for utilizing the entire spectrum of electromagnetic wave to detect sample materials. It can also be appreciated that it would be desirable to have an apparatus and method that can determine the change of effective dielectric constant by detecting the change in the power of the electromagnetic wave in the circular resonator due to the coupling of the sample materials to the circular resonator. It can also be appreciated to have an apparatus and method that can detect the change in the power of the electromagnetic wave in the circular resonator at resonance condition and/or during a build-up stage.

SUMMARY

Embodiments of the present disclosure provide an apparatus and methods for detecting a selected material that change an effective dielectric constant of a circular resonator. An example of the apparatus includes an input waveguide, an output waveguide, and a circular resonator. The input waveguide receives electromagnetic wave from an electromagnetic wave source. The circular resonator bonds to a selected material, e.g. chemical gas, chemical liquid, and bio-agent. The selected material can change the effective dielectric constant of the circular resonator, which in turn causes a change in the electromagnetic wave intensity of the circular resonator. The output waveguide receives the change in electromagnetic wave intensity from the circular resonator, which can be used to detect the selected material qualitatively and quantitatively.

In another embodiment, an apparatus for detecting a selected material that change an effective dielectric constant of a circular resonator comprises an input waveguide, an output waveguide and a circular resonator. The input waveguide can receive electromagnetic wave. The circular resonator is located adjacent to the input and output waveguides such that the electromagnetic wave is coupled in and out of the circular resonator. The circular resonator causes the electromagnetic wave to travel many times within the circular resonator during a build-up stage. A selected material that is bonded to the circular resonator interacts with the selected material many times as the electromagnetic wave travel many times within the circular resonator during the build-up stage. The interaction of the electromagnetic wave with the selected material changes the power of the electromagnetic wave in the circular resonator. The output waveguide receives the change in the power of the electromagnetic wave in the circular resonator.

In another embodiment, a method for detecting a change in effective dielectric constant of a circular resonator and, thus, the presence of a selected material, comprises inputting an electromagnetic wave into an input waveguide and coupling the electromagnetic wave received by the input waveguide to a circular resonator. The method further includes bonding a selected material to the circular resonator such that the selected material can change the power of the electromagnetic wave in the circular resonator and receiving the power of the electromagnetic wave in the circular resonator that was changed by bonding the selected material to the circular resonator.

In another embodiment, a method for detecting a selected material that change an effective dielectric constant of a circular resonator comprises inputting an electromagnetic wave into an input waveguide and coupling the electromagnetic wave received by the input waveguide to a circular resonator. The method further includes bonding a selected material to the circular resonator. The electromagnetic wave interacts with the selected material many times while traveling around the circular resonator causing a change in the power of the electromagnetic wave in the circular resonator. The method further includes receiving the electromagnetic wave in the circular resonator that was changed by bonding the selected material to the circular resonator.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
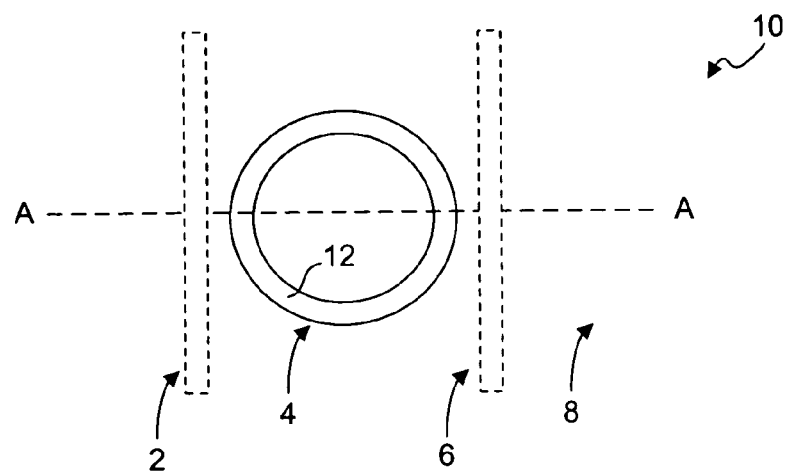
FIG. 1 is an exemplary schematic view of an embodiment of an apparatus of the present disclosure for detecting a change in effective dielectric constant in the form of a ring resonator.

Disclosed herein is an invention that uses the build-up stage and/or resonance condition of a circular resonator to detect selected materials that changes the dielectric constant of the circular resonator. The dielectric constant is a measurement of the relative effectiveness of a substance as an electrical insulator. It is a physical parameter for all materials across the entire spectrum of electromagnetic wave or light. The effective dielectric constant is the combined influence of dielectric constant when multiple substances are considered in a particular application.

At resonance condition, the effective dielectric constant of a circular resonator can be determined using formula:

$$f_i = \frac{ic}{2\pi r \sqrt{\varepsilon_{eff}}} \quad \text{or} \quad \sqrt{\varepsilon_{eff}} = \frac{i\lambda_i}{2\pi r} \tag{1}$$

where i is a positive integer, c the speed of light in a vacuum, $\varepsilon_{eff}$ the effective dielectric constant, r the radius of a circular resonator, and $\lambda$ the wavelength of the electromagnetic wave or light in the material. In general the frequency and the radius are fixed However, the dielectric constant can be determined at any frequency, which allows the use of the entire spectrum of electromagnetic wave. When the electromagnetic wave in the circular resonator is at resonance condition, this equation is used to express the effective dielectric constant of the circular resonator. Further; the electromagnetic wave in the circular resonator will have the maximum power of the electromagnetic wave at resonance condition. In general any external influence on the circular resonator causes the power of the electromagnetic wave in the circular resonator to change, typically to decrease. Thus, the present disclosure can be used to detect the presence of a selected material that changes a dielectric constant of the resonator due to the influence of the selected material on the resonator.

The interface among an input waveguide, output waveguide, and circular resonator can be adjusted so that the coupling of the electromagnetic wave in and out of the circular resonator is weak The weak coupling allows the electromagnetic wave to travel many times within the resonator. Because the electromagnetic wave travels many times within the resonator, the electromagnetic wave interacts many times with the selected material bonded on the surface of the circular resonator. The small absorption or deflection of the power of the electromagnetic wave that is caused by the selected material bonded to the circular resonator is incremented as the electromagnetic wave travels many times within the resonator. This augments the change in the power of the electromagnetic wave and can increase the sensitivity of the sensor.

The detection of the change in the power of the electromagnetic wave during the build-up stage is determined using the formula:

$$\frac{E_c}{E_i} = \frac{jt\tau \exp(j\phi)}{1 - r\tau \exp(j\phi)} \tag{2}$$

which is the ratio of the circulating field to the input field. This formula assumes that the interface among the input waveguide, output waveguide, and circular resonator weakly couples the electromagnetic wave into and out of the circular resonator. The interface can behave as a beam-splitter. From equation 2, r and t are the reflectivity and transmissivity of the beam-splitter, $\phi=\beta L$ and $\tau=\exp(-\alpha L/2)$ are the single-round-trip phase shift and transmission coefficient, $\alpha$ is the attenuation coefficient, $\beta$ is the propagation constant, L is the ring length, $E_c$ is the circulating electromagnetic wave inside the resonator and $E_i$ is the input electromagnetic wave to the waveguide.

A magnification of the ring resonator sensor structure, M, is defined as the ratio of the circulating intensity of the electromagnetic field within the resonator to the incident intensity of the electromagnetic field to the input waveguide. Therefore, the magnification of the ring resonator can be determined using formula:

$$M = \frac{I_c}{I_i} = \left|\frac{E_c}{E_i}\right|^2 = \frac{(1-r^2)\tau^2}{1 - 2r\tau\cos(\phi) + r^2\tau^2} \tag{3}$$

Equation 3 indicates that if coupling among the input and output waveguides and the circular waveguides is adjusted to be weak, the electromagnetic wave can travel many times within the circular resonator.

The present disclosure provides for the selected material to be in direct contact or in close proximity to the circular resonator to detect the selected material. Further, the sensor can form a cascade circular chain that includes at least two (2) circular resonators and/or a two dimensional array with individually accessible circular resonators that includes at least two (2) input waveguides, at least two (2) output waveguides, and at least two (2) circular resonators.

Exemplary apparatus are first discussed with reference to the figures. Although these apparatus are described in detail, they are provided for purposes of illustration only and various modifications are feasible. After the exemplary apparatus have been described, examples of operation of the apparatus are provided to explain the manner in which the sensor detects the selected materials.

Referring now in more detail to the Figures in which like numerals identify corresponding parts, FIG. 1 illustrates an exemplary circular resonator sensor 10 that detects the change in the power of the electromagnetic wave in the circular resonator 4 due to the selected material bonded to the circular resonator 4, and thus, the presence of the selected material. As indicated in this figure, the sensor 10 generally comprises an input waveguide 2, a circular resonator 4, an output waveguide 6, and substrate material 8. The input and output waveguides 2, 6 can be straight waveguides. FIG. 1 shows the circular resonator 4 can be a circular waveguide in the form of a ring, which can be referred to as a ring resonator 4. The input and output waveguides 2, 6 are substantially parallel to each other and the ring resonator 4 is located between the waveguides 2, 6. The sensor 10 further includes a cladding layer 12 attached preferably on top of the ring resonator 4. However, it should be noted that the cladding layer is not necessary to detect the selected material that changes the effective dielectric constant of the ring resonator 4.

An electromagnetic wave or light (not shown) is inputted into the input waveguide 2. The electromagnetic wave and the ring resonator 4 are fixed at a frequency and radius, respectively. The ring resonator 4 is coupled to the input and output waveguides 2, 6 such that the electromagnetic wave is coupled in and out of the ring resonator 4. The electromagnetic wave stabilizes at resonance condition in the ring resonator 4 and the electromagnetic wave is at its maximum power or intensity. Any external influence, such as the presence of a chemical substance or bio-agent on the circular resonator, causes the effective dielectric constant of the ring resonator 4 to change, which in turn causes the power or intensity of the electromagnetic wave in the ring resonator 4 to change. The output waveguide 6 receives the change in the power of the electromagnetic wave and enables the sensor to detect the selected material that is exposed to the ring resonator 4.

Biological and chemical coupling can be defined as a pair or more of substances, organic or inorganic, which have the affinity for forming joint chemical and/or biological compounds. This affinity is such that when the substances are in close proximity to the cladding layer 12 or ring resonator 4, the substances bond to the cladding layer 12 or ring resonator 4 through ionic or covalent bonds or that through other molecular bonding mechanisms. A preferred method of sensing is to bond one half of an affinity pair to a sensing device which will sense one or more physical changes such as mass, or change in dielectric properties when the matching half of the affinity pair links with the first half bonded to the sensor. The change in physical property is recorded as a sensing event.

An example of an inorganic sensing pair can be given by a carbon monoxide sensors using metals such as palladium and molybdenum which provide measurable changes depending o the concentration of carbon monoxide in a given volume of air. The following affinity pair can illustrate organic or biological sensing. Prostate specific antigen, PSA, is detected by coupling a biological substance, such as an antibody specific to the PSA, on to the sensing device. The biological substance is typically combined with an alkyl or thiol group. The alkyl and thiol groups form attachments to silicon and gold surfaces respectively. Should the PSA antigen bind with the PSA antibody, the resulting combination produces different molecular compounds with results in a physical change such as increased mass or other perturbation, which can be recorded as a sensing event.

The selected material can include chemical substances or bio-agents that are in close proximity to the ring resonator 4. More particularly, the chemical substance or bio-agents can be in direct contact with the ring resonator 4 or with the cladding layer 12. The selected material can be detected by detecting the change of power or intensity of the electromagnetic wave in the ring resonator 4, which reflects the change in effective dielectric constant of the cladding layer 12 of the ring resonator 4 when exposed to certain chemical substances or bio-agents. For example, a bio-agent can bond to the top of the cladding layer of the ring resonator 4 and cause the power of the electromagnetic wave in the ring resonator 4 to change, which is received at the output waveguide 6. The change in the power of the electromagnetic wave can be used to detect the selected material.

Alternatively, the selected material can be detected by detecting change of power or intensity of the electromagnetic wave in the ring resonator 4 without the cladding layer 12. In this instance, the selected material is bonded directly to the ring resonator 4 when exposed to certain chemical substances or bio agents. For example, a bio agent can bond to the ring resonator 4 and cause the power of the electromagnetic wave in the ring resonator to change. The change in the power of the electromagnetic wave is received by the output waveguide 6 and can be used to detect the selected material.

Figure 2:
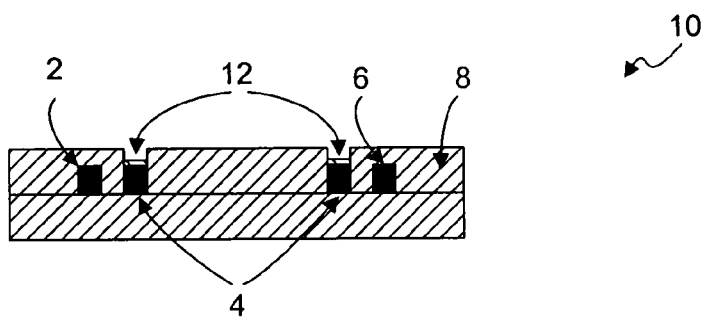
FIG. 2 is a cross section view along line AA of FIG. 1.

FIG. 2 is a cross section view along line AA of FIG. 1 and shows a circular resonator sensor 10 that includes a cladding layer 12. When the selected material e.g., the chemical gas/liquid or bio-agent, is exposed to the resonator 4, the selected material bonds to the cladding layer 12 causing the power of the electromagnetic wave in the ring resonator 4 to change. Further, the selected material can bond directly or in close proximity to the cladding layer 12. The change in the power of the electromagnetic wave reflects the change in the dielectric constant of the cladding layer 12 and enables the sensor to provide information about the selected material. The cladding layer 12 can be comprised of gold oxide, silicon oxide, silicon nitride, oxynitride or any silicon base. In general any metal oxide can be used with the cladding layer as long as their dielectric constants are less than that of the waveguide materials and their absorption coefficiencies are not too large such that the metal oxide absorbs all the electrical fields in the waveguide area. It should be noted that the sensor 10 may or may not include the cladding layer 12 to detect the selected material.

Figure 3:
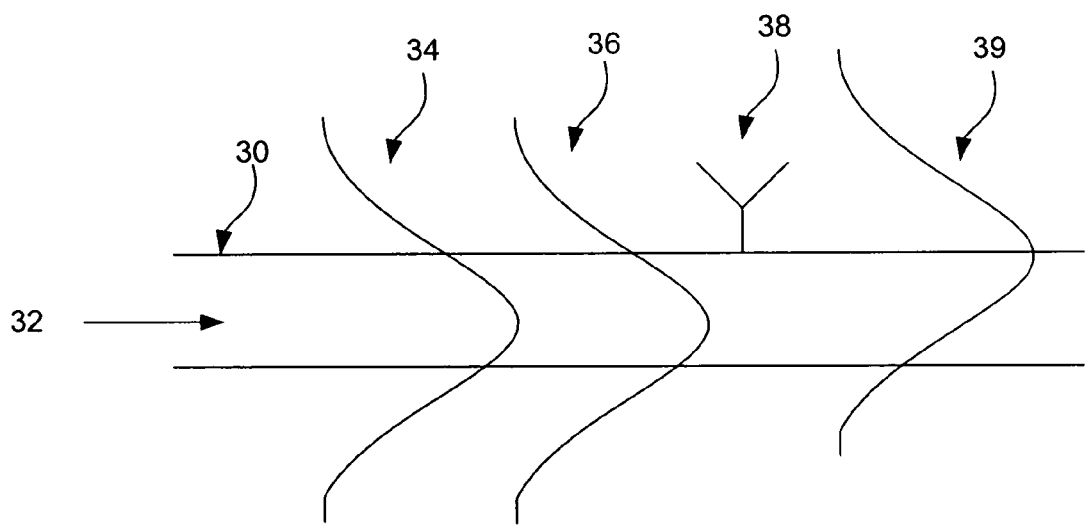
FIG. 3 is an exemplary diagram depicting a change in the power of the electromagnetic wave in a circular resonator embodiment of the present disclosure when the circular resonator is exposed to selected materials.

FIG. 3 illustrates the effects of a selected material 38 when bonded to a circular resonator 30. At resonance condition, electromagnetic wave 32 is coupled to the circular resonator 30 and has its maximum power in the circular resonator 30. The amplitudes 34 and 36 represent the maximum power of the electromagnetic wave 32 contained in the circular resonator 30 at resonance condition. When the selected material 38 is bonded to the circular resonator 30, the power of the electromagnetic wave changes resulting in a shift of amplitude as shown in reference numeral 39. In general, the selected material 38 absorbs and deflects the electromagnetic wave 32 causing the power of the electromagnetic wave 32 to change, typically to decrease.

The power of electromagnetic wave 32 is coupled into and out of the circular resonator 30 through the input and output waveguides. When the circumference of the circular resonator 30 is equal to an integral multiple of a guided wavelength, resonance is established. This is expressed as $$2\pi r = n\lambda_g, \text{ for } n=1, 2, 3, \qquad (4)$$

where r is the radius of the circular resonator, $\lambda_g$ is the guided wavelength, and n is the mode number. The guided wavelength, $\lambda_g$, can be related to the vacuum wavelength and frequency by $$\lambda_g = \frac{\lambda}{\sqrt{\varepsilon_{eff}}} = \frac{c}{f * \sqrt{\varepsilon_{eff}}} \qquad (5)$$

where c is the speed of light, $\lambda$ and f are the fixed wavelength and fixed frequency of the electromagnetic wave in vacuum, respectively, and $\varepsilon_{eff}$ is the effective dielectric constant. When the electromagnetic wave is stabilized at resonance condition, equations (5) and (6) become $$2\pi r \sqrt{\varepsilon_{eff}} = n\lambda, \text{ for } n=1, 2, 3, \qquad (6)$$

at which the input power with fixed wavelength of $\lambda$ is coupled into and out of the circular resonator 30 at its maximum. Therefore, the power of the electromagnetic wave 32 in the circular resonator 30 is at its highest.

When the effective dielectric constant changes due to external influences and the wavelength of the electromagnetic wave 32 is fixed, the resonance condition is lost and the output power of the electromagnetic wave in the circular resonator 30 is typically reduced. In addition, the rate of power level reduction depends on the changing rate of the dielectric constant and the coupling efficiency of the circular resonator 30.

For example, referring to FIG. 3, when the foreign agent 38 bonds to the surface of the circular resonator 30, the effective dielectric constant becomes the joint contribution of the foreign agent 38 and the circular resonator 30. The bonding of the foreign agent 38 to the surface of the circular resonator 30 destroys the balance of the equation (6), typically reducing the output power of the electromagnetic wave 32 in the circular resonator 30. Similarly the effective dielectric constant of the circular resonator 30 can be altered by foreign radiation, e.g., laser illumination or electron beam processing. The alteration of the effective dielectric constant causes an imbalance of the equation (6) and typically reduces the output power of the electromagnetic wave 32 in the circular resonator 30.

The present invention can also detect a selected material that changes an effective dielectric constant of a circular resonator during a build-up stage. The electromagnetic wave can travel many times within the circular resonator as explain with reference to equation 4. The electromagnetic wave can interact with the selected material bonded to the circular resonator many times during the build-up stage. Each time the electromagnetic wave interacts with the selected material as it circulates the resonator, the small absorption or deflection of the power of the electromagnetic wave is augmented. For example, referring to FIG. 3, the power of the electromagnetic wave 32 is shifted as shown in reference 39 as a result of one of the many times the electromagnetic wave travels within the circular resonator. When the electromagnetic wave circulates for the nth time within the circular resonator, the power of the electromagnetic wave is shifted or the change is magnified for the nth time that the electromagnetic wave circulates the resonator. In this way, the small absorption or deflection caused by a small perturbation in the circular (sensing) area will be built-up and transferred into a much larger change in the power of the electromagnetic wave. Thus, the sensitivity of the sensor is increased. Further, a magnification of the circular resonator sensor can be adjusted to reach as high as $10^4$.

Based on the change in the power of the electromagnetic wave of the circular resonator, the sensor can detect the selected material quantitatively or qualitatively. For example, a certain quantity of a selected material may be known to yield a certain power change of the electromagnetic wave. Thus, a range of the quantity of the selected material can be determined. Alternatively, a quality of a selected material can be determined from the characteristic of a cladding layer. For example, the cladding layer can have a characteristic that only bonds with a certain selected material. If the selected material bonds with the cladding layer, the power of the electromagnet wave changes indicating the quality of the selected material. Other ways of determining the quantity and the quality of the selected material are known to those skilled in the art.

Figure 4:
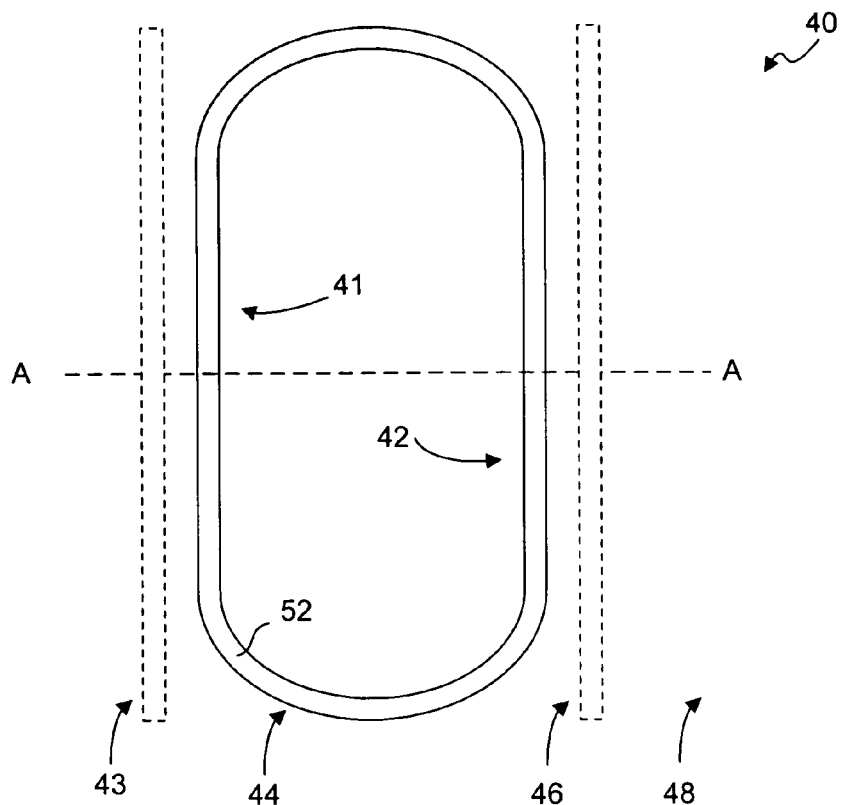
FIG. 4 is an exemplary schematic view of another embodiment of an apparatus of the present disclosure for detecting a change in effective dielectric constant in the form of a racetrack resonator.

FIG. 4 shows an embodiment of the circular resonator sensor in a form of a racetrack. The racetrack resonator sensor 40 includes an input waveguide 43, a racetrack resonator 44, and an output waveguide 46, a cladding layer 52, and a substrate material 48. The racetrack resonator sensor 40 functions similarly to the ring resonator as shown in FIG. 1. Referring to FIG. 4, the input and output waveguides 43, 46 are substantially straight waveguides. The racetrack resonator 44 further includes at least one substantially straight waveguide section 41, 42 that provides more surface area for the input and output waveguides 43, 46 to couple the electromagnetic waves in and out of the racetrack resonator 44. This is relative to the ring resonator 4 of FIG. 1. Further, the input and output waveguides 43, 46 can be configured to conform substantially to the configuration of the racetrack resonator 44 to provide a greater surface area for coupling of the electromagnetic waves.

Figure 5:
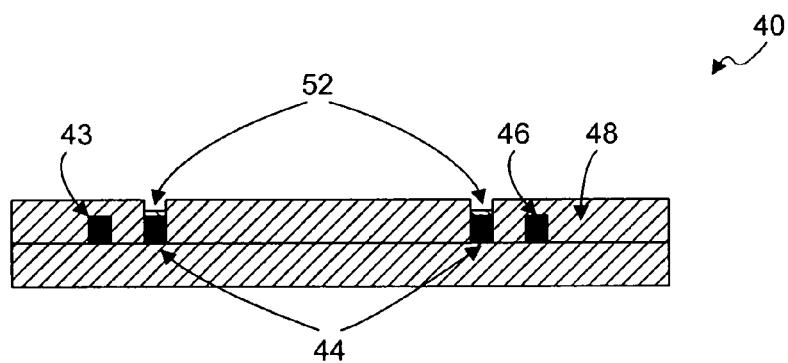
FIG. 5 is a cross section view along line AA of FIG. 4.

FIG. 5 is a cross section view along line AA of FIG. 4. The cross section view of the racetrack sensor 40 further illustrates the racetrack resonator 44, which includes a cladding layer 52. The selected material can bond to the cladding layer of the racetrack resonator 44 changing the power of the electromagnetic wave in the resonator 44, which reflects the change in the effective dielectric constant of the cladding layer 52 and the resonator 44. The change enables the racetrack resonator sensor 40 to detect the selected materials quantitatively and qualitatively. It should be noted that the racetrack resonator 44 may or may not include the cladding layer 52 in order to determine the effective dielectric constant.

Figure 6:
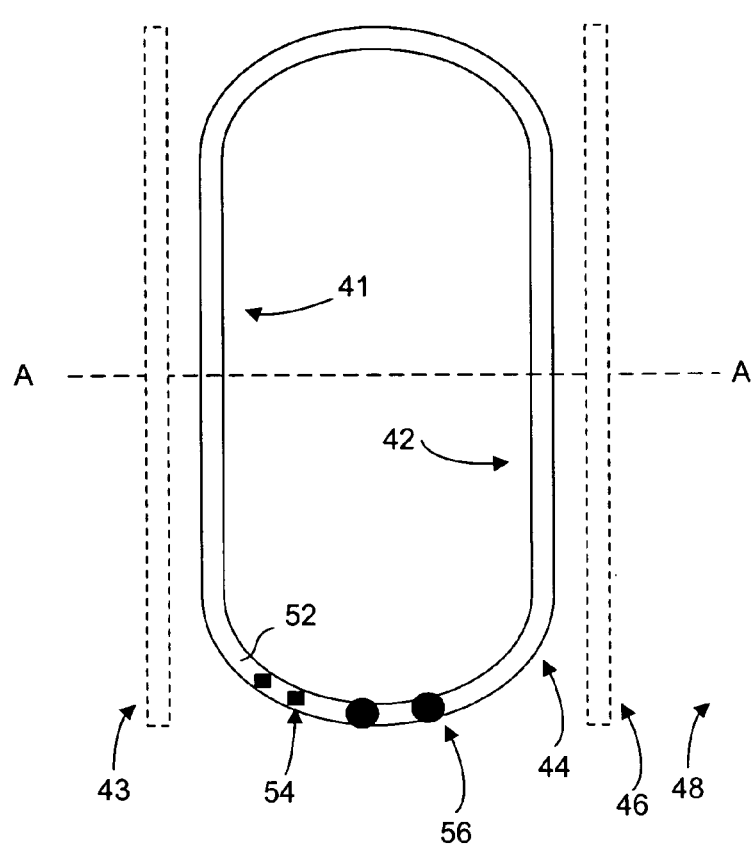
FIG. 6 is a schematic view of the embodiment of FIG. 4 exposed to selected materials.

FIG. 6 shows a racetrack resonator sensor 40 that is exposed to selected materials, e.g., unbound or bound biological affinity agents, such as antibodies 54 and antibodies 56 complexed with antigens. The racetrack resonator sensor 40 of FIG. 6 includes an input waveguide 43, a racetrack resonator 44, an output waveguide 40, a cladding layer 52, and a substrate material 48. The agents 54, 56 can bond to the cladding layer 52, and thus, absorb and deflect the power of the electromagnetic wave in the resonator 44 causing the power to change, as described with reference to FIG. 3. Alternatively, the sensor 40 can function without the cladding layer 52. The agents can bond to the resonator 44 instead of the cladding layer 52. The agents absorb and deflect the power of the electromagnetic wave in the resonator 44 causing the power to change, as described with reference to FIG. 3. The detection of the change in the power of the electromagnetic wave reflects the change in the effective dielectric constant of either the resonator 44 or the cladding layer 52 of the resonator 44 and enables the sensor 40 to detect the agents 54, 56 quantitatively and qualitatively.

Figure 7:
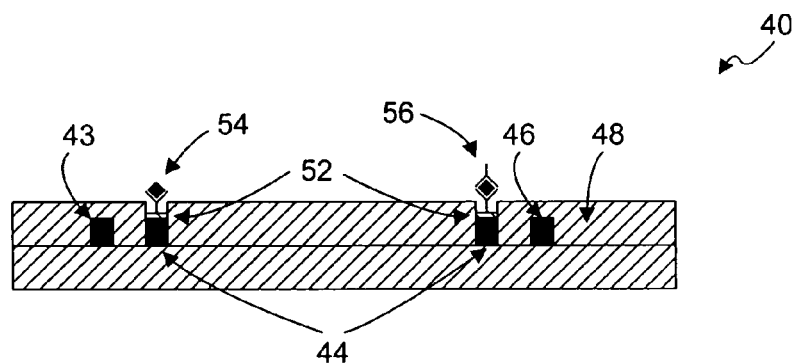
FIG. 7 is a cross section view along lines AA of FIG. 6, illustrating the coupling of selected materials on the racetrack resonator as shown in FIG. 5.

FIG. 7 is a cross section view along line AA of FIG. 6 illustrating an example of the unbound biological affinity agents 54, such as antibodies, and bound biological affinity agents 56 such as antibodies complexed with antigens bonded to the racetrack resonator 44. The agents 54, 56 can be bonded to the racetrack resonator 44 or cladding layer 52 of the racetrack resonator 44. The agents 54, 56 can be bonded directly or in close proximity to the resonator 44 or the cladding layer 52, resulting in an absorption and deflection of the electromagnetic wave power in the racetrack resonator 44. The absorption and deflection change the power of the electromagnetic wave in the resonator 44, which is received by output waveguide 46. The change in the power of the electromagnetic wave enables the sensor 40 to detect the selected material quantitatively and qualitatively.

Figure 8:
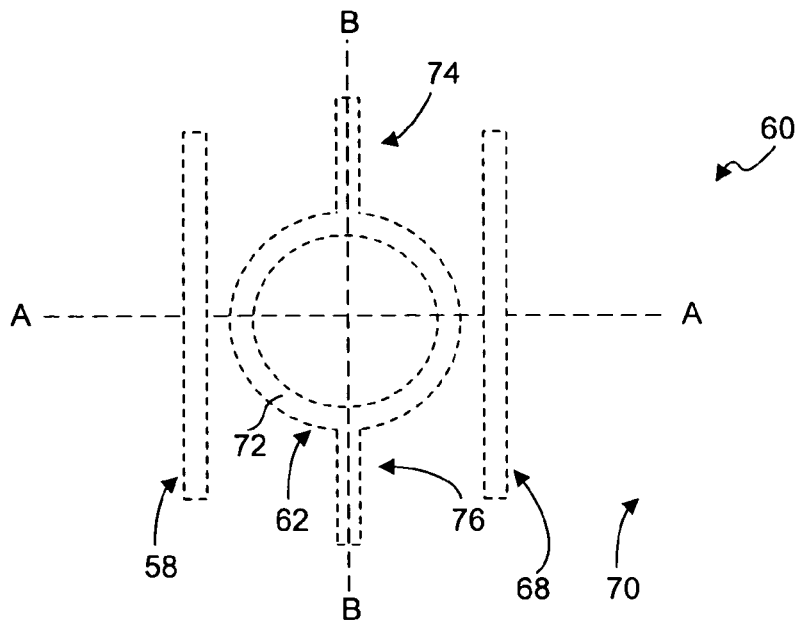
FIG. 8 is an exemplary schematic view of an embodiment of an apparatus for detecting a change in dielectric constant of a circular resonator, in which selected materials flow along the circular resonator.

FIG. 8 illustrates a circular resonator sensor 60 that has a microfluidic channel 72 that can be placed on top of a ring resonator 62 such that chemical substances or bio-agents can pass through the channel and interact with the ring resonator 62. In this embodiment, the ring resonator sensor 60 further includes an input waveguide 58, an output waveguide 68, and a substrate material 70. The microfluidic channel 72 includes an input port 74 where the selected material is introduced into the channel and an output port 76 where the selected material exits out of the channel of the sensor 60. As the selected material passes through the channel 72, the selected material bonds to the ring resonator 62 and changes the power of the electromagnetic wave in the ring resonator 62. The change in the power of the electromagnetic wave is received by the output waveguide 68 and enables the sensor 60 to detect selected material quantitatively and qualitatively.

Figure 9:
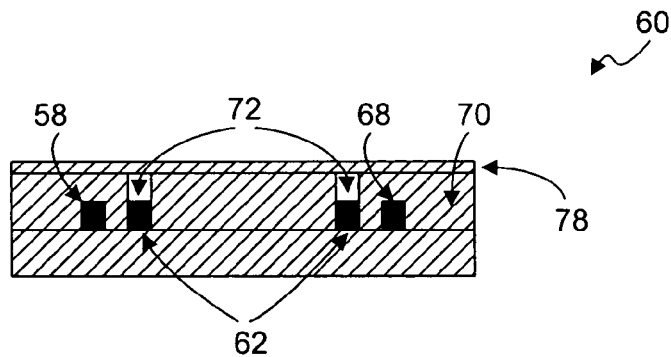
FIG. 9 is a cross section view along line AA of FIG. 6.
Figure 10:
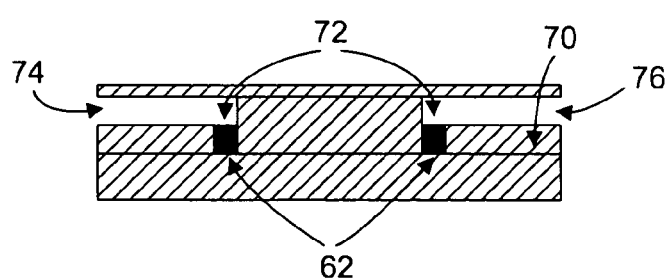
FIG. 10 is a cross section view along line BB of FIG. 6.

FIG. 9 illustrates a cross section view along lines AA of FIG. 8. The cross section view of the ring resonator sensor 60 is similar to the cross section view as shown in FIG. 5. The cross section view of FIG. 9 further includes a top layer 78 that is placed on top of the microfluidic channel 72. FIG. 9 does not show a cladding layer, but the ring resonator 62 may or may not include the cladding layer. FIG. 10 is another cross section view of FIG. 8 that is along line BB of FIG. 8, axially along the input and output ports 74, 76.

Figure 11:
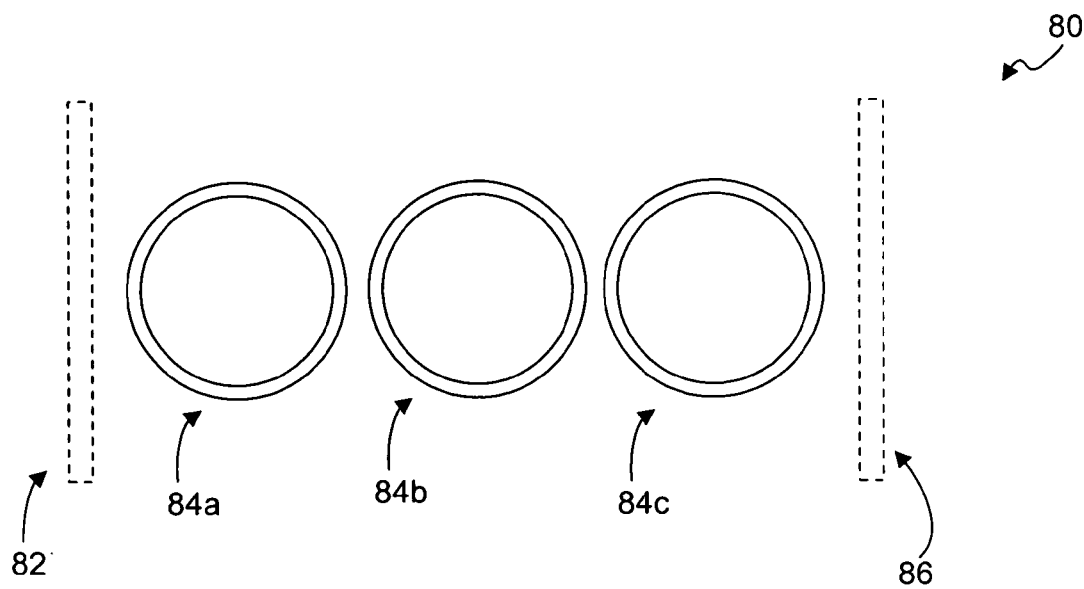
FIG. 11 is an exemplary embodiment of a circular sensor of the present disclosure in a cascade arrangement.

FIG. 11 illustrates an exemplary embodiment of a cascade arrangement of circular resonators 84a–c. The cascade circular resonator sensor 80 includes an input waveguide 82, a plurality of circular resonators 84a–c in a cascade arrangement, and an output waveguide 84. Selected materials can be exposed to at least one of the plurality of circular resonators 84 to change the power of the electromagnetic wave in the resonators 84. In addition, different types of selected materials can be exposed to each of the circular resonators 84 in the cascade circular resonators sensor 80.

Figure 12:
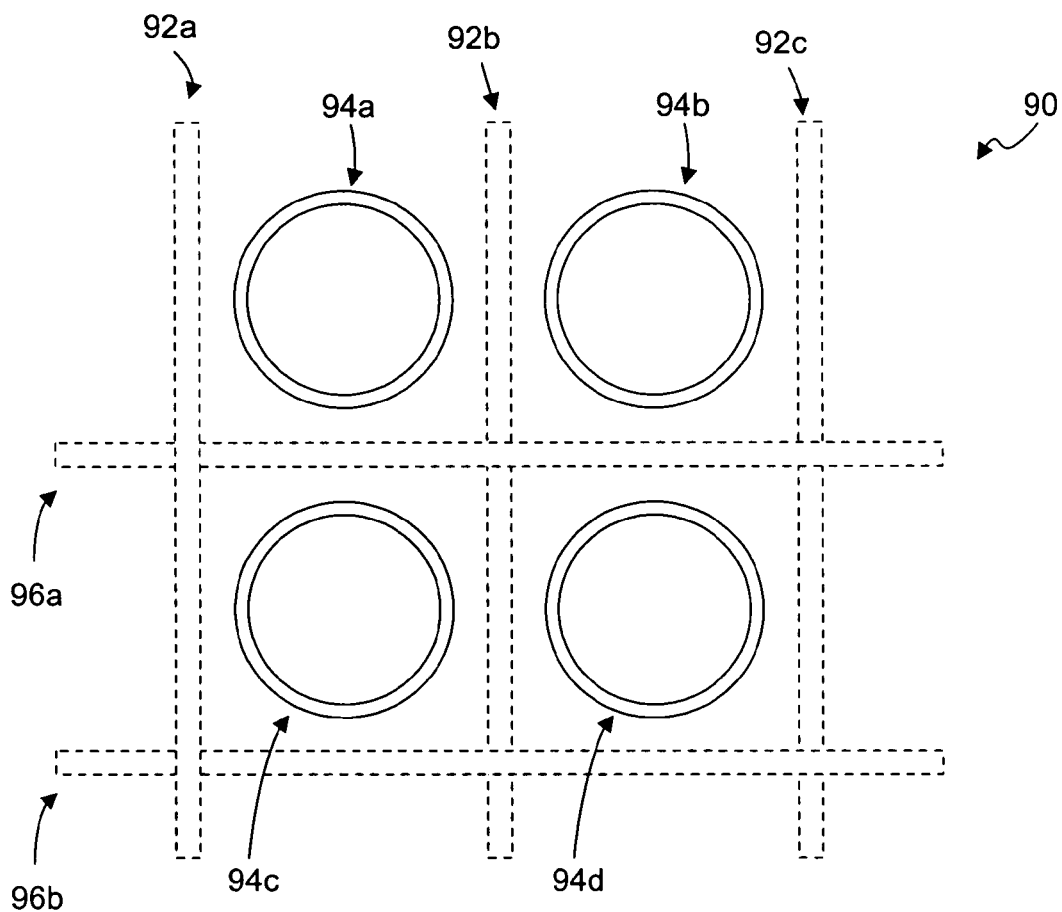
FIG. 12 is an exemplary embodiment of a circular sensor of the present disclosure in an array arrangement.

FIG. 12 illustrates exemplary embodiment of an array circular resonator sensor 90. The array sensor 90 includes at least two input waveguides 92a–c, at least two circular resonators 94a–d, and at least two outport waveguides 96a–b. The multiple input waveguides 92a–c can be inputted with different electromagnetic wave forms that can be used to detect multiple selected materials and can further discriminate against interferences. The array sensor 90 can be designed to provide multiple data points per selected material, which can provide additional information about the selected material. The multiple input waveguides 92a–c can be arranged in columns and the multiple output waveguides 96a–b can be arranged in rows, as shown in FIG. 12. Further, the circular resonators 94a–d can be placed between the rows and columns of the input waveguides 92a–c and output waveguides 96a–b. For example, resonator 94a can be placed in the center of input waveguides 92a, 92b, and output waveguide 96a and the circular resonator 94c can be placed in the center of output waveguides 96a, 96b, and input waveguides 92a, 92b. The array sensor 90 can be based on a single material class on a single type of sensor platform, or various types of materials combined with one or more sensor platforms.

It should be noted that the sensors 10, 40, 60, 80, and 90 can be designed and fabricated into an integrated chip. The sensors can also be integrated with semiconductor circuits so that the sensors can be electronically accused and controlled with, for example, a data acquisition system. Further, the sensor 10, 40, 60, and 80 can include more than one input waveguides and more than one output waveguides. The waveguides can be arranged anywhere about the XYZ coordinates as long as the electromagnetic wave couples in and out of the resonator.

Figure 13:
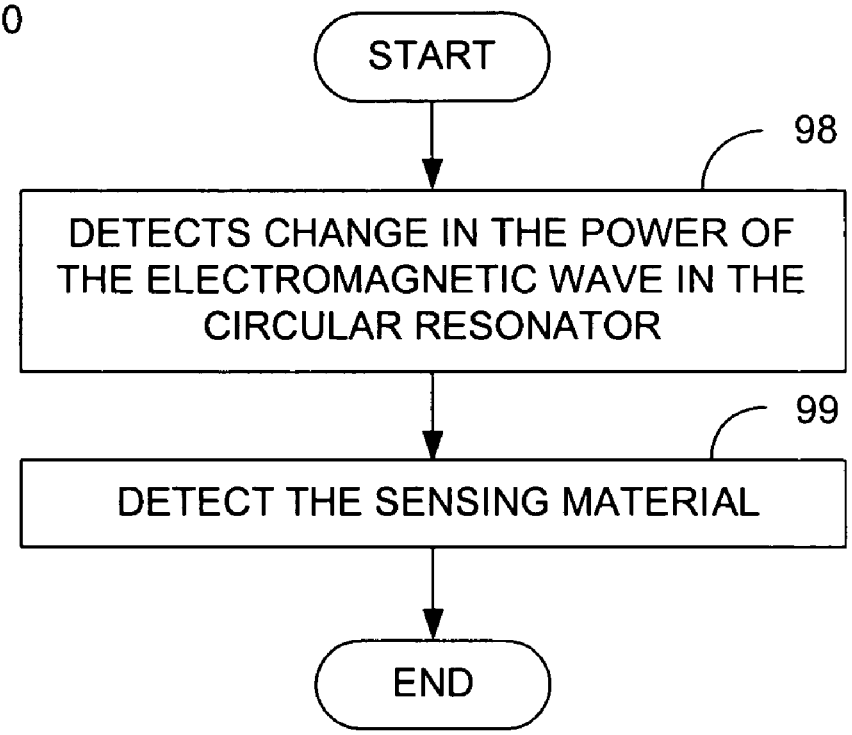
FIG. 13 is an exemplary flow chart illustrating the general operation of sensors 10, 40, 60, 80, 90 of FIGS. 1, 4, 8, 11 and 12.

FIG. 13 is a high level flowchart of sensors 10, 40, 60, 80, and 90 shown in FIGS. 1, 4, 8, 11, and 12. Referring to block 98, the sensors 10, 40, 60, 80, and 90 detect the change in the power of the electromagnetic waves in the circular resonator. In block 99, the sensors 10, 20, 40, 60, 80, and 90 detects the selected material.

Figure 14:
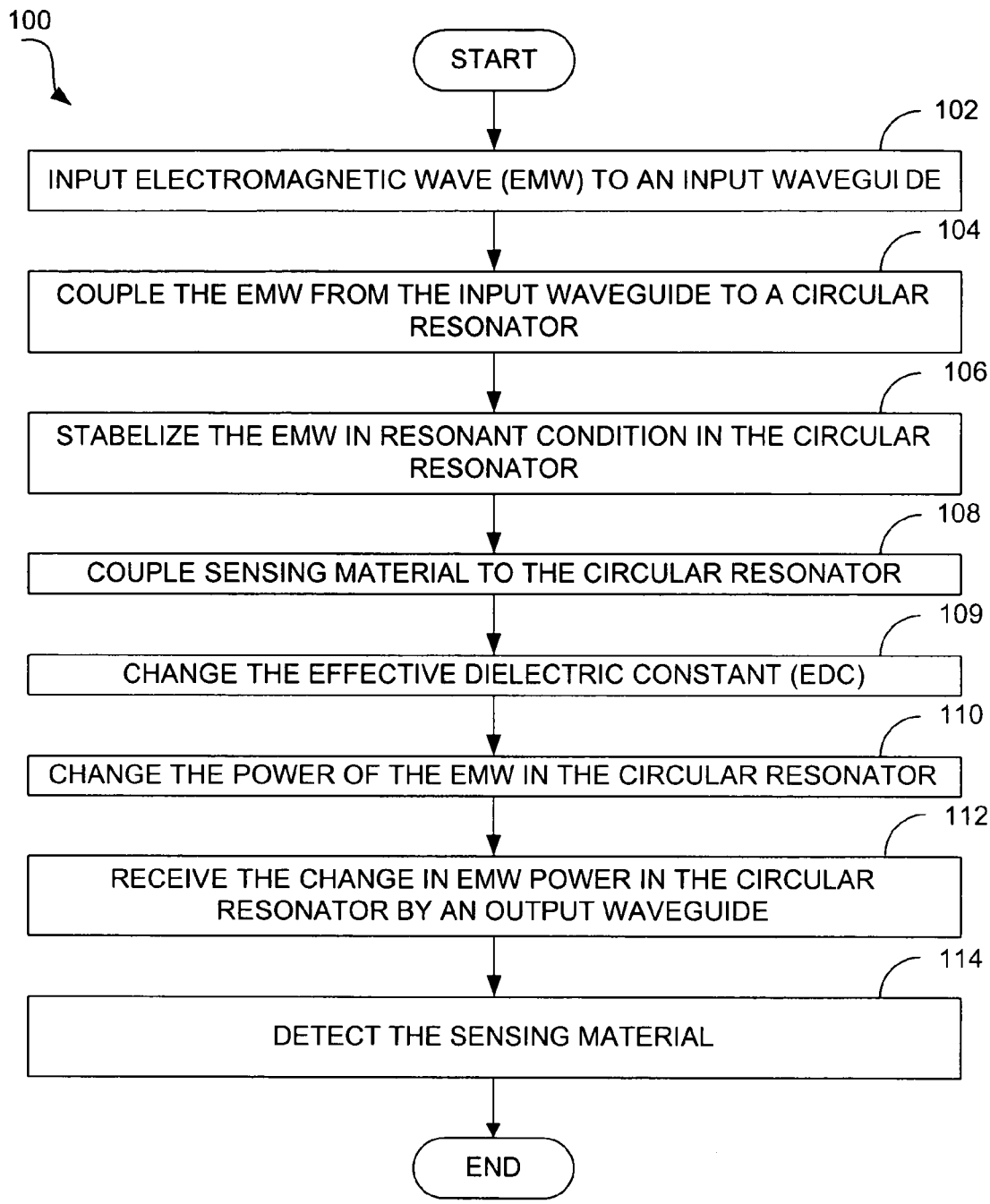
FIG. 14 is a flow chart illustrating an exemplary operation of a circular resonator sensor embodiment of the present disclosure.

FIG. 14 shows a flow diagram of an exemplary operation 100 of the circular resonator sensors 10, 20, 40, 60, 80, and 90. In block 102, an electromagnetic wave is inputted into an input waveguide from an electromagnetic wave source. The electromagnetic wave is coupled from the input waveguide to a circular resonator, as shown in block 104. The electromagnetic waveguide stabilizes at resonant condition in the circular resonator, as shown in block 106, in which the power of the electromagnetic wave is at its maximum. Alternatively, the electromagnetic wave circulates within the circular resonator many times during a build-up stage.

A selected material is introduced to the circular resonator. The selected material bonds to the circular resonator, as shown in block 108. The bonding of the selected material to the circular resonator can be a direct contact or a close proximity to the circular resonator. Alternatively, the bonding of the selected material to the circular resonant can also include bonding the selected material to the cladding layer of the circular resonator.

Once the selected material bonds to the circular resonator or the cladding layer, the effective dielectric constant of the circular resonator (or the cladding layer/circular resonator) changes as shown in block 109. The power of the electromagnetic wave changes in the circular resonator, which usually results in a decrease in the power of the electromagnetic wave, as shown in block 110. The change in the electromagnetic wave power in the circular resonator is received by an output waveguide, as shown in block 1112. The change in the electromagnetic wave power reflects the change in effective dielectric constant of the circular resonator and enables the sensor to detect the selected material qualitatively and/or quantitatively, as shown in block 114.

It should be emphasized that the above-described embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The invention claimed is:

1. An apparatus for detecting a selected material that changes an effective dielectric constant of a circular resonator, the apparatus comprising:
    an input waveguide being capable of receiving electromagnetic wave;
    an output waveguide; and
    a circular resonator located adjacent to the input and output such that the electromagnetic wave is coupled in and out of the circular resonator, the resonator being capable of bonding to the selected material such that the selected material changes the power of the electromagnetic wave in the circular resonator, wherein the output waveguide receives the change in the power of the electromagnetic wave in the circular resonator.

2. The apparatus as defined in claim 1, wherein the circular resonator causes the electromagnetic wave to travel many times within the circular resonator during a build-up stage, the electromagnetic wave being interactive with the selected material many times causing the change in the power of the electromagnetic wave in the circular resonator.

3. The apparatus as defined in claim 1, wherein the electromagnetic wave stabilizes at resonance condition in the circular resonator and the selected material bonded to the circular resonator causes the power of the electromagnetic wave at resonance condition in the circular resonator to change.

4. The apparatus as defined in claim 1, wherein the input and output waveguides are substantially straight.

5. The apparatus as defined in claim 1, wherein the circular resonator is shaped as one of a ring and racetrack waveguide.

6. The apparatus as defined in claim 1, wherein the selected material is one of a chemical substance and bio-agent.

7. The apparatus as defined in claim 1, wherein the circular resonator further comprises a cladding layer, wherein the selected material is capable of changing the dielectric constant of the cladding layer.

8. The apparatus as defined in claim 1, wherein the input and output waveguides are substantially parallel to each other and the circular resonator is located between the waveguides.

9. The apparatus as defined in claim 1, wherein the resonator being capable of bonding to the selected material is in direct contact or in close proximity with the selected material.

10. The apparatus as defined in claim 1, further comprising another circular resonator located adjacent to the circular resonator and between the waveguides forming a cascade arrangement.

11. The apparatus as defined in claim 1, further comprising a fluidic channel that the selected material can pass through and interact with the circular resonator.

12. The apparatus as defined in claim 1, further comprising:
    another circular resonator;
    another input waveguide; and
    another output waveguide, wherein the input waveguides are arranged substantially in parallel to each other, the output waveguides are arranged substantially in parallel to each other and substantially perpendicular to the parallel input waveguides, the circular resonators being located in the center of the input and output waveguides forming an array arrangement.

13. A method for detecting a selected material that changes an effective dielectric constant of a circular resonator, the method comprising the steps of:
    inputting an electromagnetic wave into an input waveguide;
    coupling the electromagnetic wave received by the input waveguide to a circular resonator;
    bonding the selected material to the circular resonator such that the selected material changes the power of the electromagnetic wave in the circular resonator; and
    receiving electromagnetic wave in the circular resonator that was changed by the bonding of the selected material to the circular resonator.

14. The method as defined in claim 13, further comprising causing the electromagnetic wave to travel many times within the circular resonator during a build-up stage, wherein the electromagnetic wave interacts with the selected material many times causing the change in the power of the electromagnetic wave in the circular resonator.

15. The method as defined in claim 13, further comprising stabilizing the electromagnetic wave at resonance condition in the circular resonator, wherein the selected material bonded to the circular resonator causes the power of the electromagnetic wave at resonance condition in the circular resonator to change.

16. The method as defined in claim 13, further comprising bonding the selected material to a cladding layer of the circular resonator, wherein the selected material is capable of changing the dielectric constant of the cladding layer.

17. The method as defined in claim 13, wherein attaching the selected material to the circular resonator further comprises the selected material being in direct contact or in close proximity with the circular resonator.

18. The method as defined in claim 13, further comprising providing another resonator forming a cascade arrangement.

19. The method as defined in claim 13, further comprising providing another resonator, another input waveguide and another output waveguide forming an array arrangement.

20. The method as defined in claim 13, wherein the input and output waveguides are substantially straight.

21. The method as defined in claim 13, wherein the circular resonator is one of a ring or racetrack resonator.

22. The method as defined in claim 13, further comprising providing a fluidic channel located on top of the circular resonator.

23. The method as defined in claim 13, further comprising providing a cladding layer to the circular resonator.

24. The method as defined in claim 13, further comprising placing the input and output waveguides substantially in parallel to each other and placing the circular resonator between the waveguides.

25. A method for detecting the presence of a chemical or bio-agent, the method comprising the steps of:
    inputting an electromagnetic wave into an input waveguide;

coupling the electromagnetic wave received by the input waveguide to a circular resonator;

bonding the chemical or bio-agent to the circular resonator such that the chemical or bio-agent changes the power of the electromagnetic wave in the circular resonator; and receiving electromagnetic wave in the circular resonator that was changed by the bonding of the chemical or bio-agent to the circular resonator.

26. The method as defined in claim 25, further comprising causing the electromagnetic wave to travel many times within the circular resonator during a build-up stage, wherein the electromagnetic wave interacts with the selected material many times causing the change in the power of the electromagnetic wave in the circular resonator.

27. The method as defined in claim 25, further comprising stabilizing the electromagnetic wave at resonance condition in the circular resonator, wherein the selected material bonded to the circular resonator causes the power of the electromagnetic wave at resonance condition in the circular resonator to change.

28. The method as defined in claim 25, further comprising bonding the chemical or bio-agent to a cladding layer of the circular resonator, wherein the chemical or bio-agent is capable of changing the dielectric constant of the cladding layer.

29. The method as defined in claim 25, wherein bonding the chemical or bio-agent to the circular resonator further comprises the chemical or bio-agent being in direct contact or in close proximity with the circular resonator.

30. The method as defined in claim 25, further comprising providing another resonator forming a cascade arrangement.

31. The method as defined in claim 25, further comprising providing another resonator, another input waveguide and another output waveguide forming an array arrangement.

32. The method as defined in claim 25, wherein the input and output waveguides are substantially straight.

33. The method as defined in claim 25, wherein the circular resonator is one of a ring or racetrack resonator.

34. The method as defined in claim 25, further comprising providing a fluidic channel located on top of the circular resonator.

35. The method as defined in claim 25, further comprising providing a cladding layer to the circular resonator.

36. The method as defined in claim 25, further comprising placing the input and output waveguides substantially in parallel to each other and placing the circular resonator between the waveguides.

* * * * *